United States Patent [19]

Umezawa et al.

[11] 4,395,402

[45] Jul. 26, 1983

[54] ANALGESIC AGENT

[75] Inventors: Hamao Umezawa; Tomio Takeuchi, both of Tokyo; Takaaki Aoyagi, Fujisawa; Mitsugu Hachisu, Tokyo; Kenji Kawamura, Ohiso; Shunzo Fukatsu; Yasuharu Sekizawa, both of Tokyo, all of Japan

[73] Assignee: Zaidan Hojin Biseibutsu Kagaku Kankyu Kai, Japan

[21] Appl. No.: 303,938

[22] Filed: Sep. 21, 1981

[30] Foreign Application Priority Data

Sep. 24, 1980 [JP] Japan .................................. 55-131583

[51] Int. Cl.³ .............................................. A61K 37/00
[52] U.S. Cl. .................................................... 424/177
[58] Field of Search .................. 260/112.5 R; 424/177

[56] References Cited

U.S. PATENT DOCUMENTS 4,052,449 10/1977 Umezawa et al. ............ 260/112.5 R
4,087,520 5/1978 Braun et al. ......................... 424/177

OTHER PUBLICATIONS

J. Med. Chem., (1977), vol. 20, pp. 510–515.
Chem. Abstr., vol. 96, (1982), 85947u, 68518n.
Biol. Abstr., vol. 73, 26615, (1982).

Primary Examiner—Delbert R. Phillips
Attorney, Agent, or Firm—Larson and Taylor

[57] ABSTRACT

A new analgesic agent is now provided, which comprises as the active ingredient 3-amino-2-hydroxy-4-phenylbutanoic acid and some related compounds thereof. These compounds have now found to be effective as inhibitor against enkephalinase and as an agent for enhancing analgesic activity of morphine.

6 Claims, No Drawings

ANALGESIC AGENT

SUMMARY OF THE INVENTION

This invention relates to a new analgesic agent comprising 3-amino-2-hydroxy-4-phenylbutanoic acid or some related compounds thereof which exhibit a significant activity inhibitory to the enzymatic activity of enkephalinase and enhances the analgesic activity of morphine when administered as the analgesic.

BACKGROUND OF THE INVENTION

It is known that enkaphalin or endorphine as the analgesic peptide exists in the brain of mammalian animals and particularly enkaphalin is existing at a high level in the vesicles of the nervous cells at the nerve ending of the nerve fibre in the brain, and also that enkephalinase is co-existing in the same areas as those where the enkephalin is found. Besides, the possibility that enkaphalin functions as neurotransmitters in the central nervous system of mammalian animals is suggested in the "Nature" Vol. 276, pages 523 to 526 (1980).

Furthermore, it has been revealed that acupuncture analgesia is mediated through release of the analgesic peptides such as enkephalin in the brain when the effectiveness of acupuncture analgesia was examined by measuring tail-flick latency of rats while the contents of the analgesic peptides in the brain were determined (see the Japanese medicinal Journal "Showa Igakukai Zasshi" Vol. 39, No. 5, pages 537 to 542 (1979). It is also reported that the analgesic activity of morphine is relying on that morphine plays a role to cause enkephalin to be released in the nervous system (see the "Life Science" No.25, pages 53 to 60 (1979)).

We have taken the above facts into consideration and we take it that generally, an inhibitor against enkephalinase will show an analgesic activity when it is used alone and it is expected that the inhibitor against enkephalinase will be highly effective for eliminating or minimizing the pain of such patients who feel chronic pain. In view of the disclosure in the "Showa Igakukai Zasshi" Vol. 39, No.5, pages 543 to 550 (1979), it is also expected that an enkephalinase-inhibitor will be useful as an aid for enhancing the acupuncture analgesia and morphine analgesia, and that such enkephalinase-inhibitor, even alone, will be effective to change the acupuncture-ineffective patients into the acupuncture-effective patients.

In an attempt to provide a new analgesic agent, therefore, we have extensively researched on the inhibitory activity of many known compounds against enkephalinase, the enzyme of degrading enkephalin. As a result, we have now found that 3-amino-2-hydroxy-4-phenylbutanoic acid and some related compounds thereof have the enkephalinase-inhibiting activity in vitro and, when tested in animals, exhibit the analgesic activity in vivo. Based on these our findings, we have completed this invention.

An object of this invention is to provide a new pharmaceutical composition which is useful as an analgesic agent or antinociceptive agent when used alone and which is useful to enhance the analgesic activity of morphine when it is administered in association with morphine. Another objects and utilities of this invention will be clear from the following descriptions.

DETAILED DESCRIPTION OF THE INVENTION

According to the broadest aspect of this invention, therefore, there is provided a pharmaceutical composition, useful as analgesic agent, which comprises as the active ingredient, a compound of the formula (I):

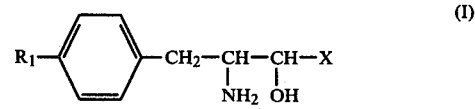

wherein $R_1$ denotes a hydrogen atom or a hydroxyl group, X denotes a group —$COR_2$ where $R_2$ is a hydroxyl group, a lower alkoxyl group, a benzyloxy group, an amino group or a lower alkyl mono- or di-substituted amino group, or X denotes a group —$CH_2OH$, a group

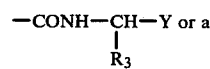

group 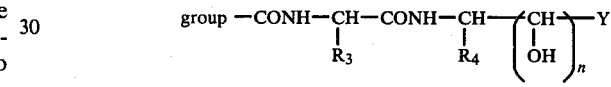

where $R_3$ and $R_4$ are equal to each other or are different from each other and are each a hydrogen atom, an alkyl group of 1 to 7 carbon atoms, a hydroxyalkyl group containing 1 to 7 carbon atoms, a mercaptoalkyl group containing 1 to 7 carbon atoms, a carboxamidoalkyl group containing 2 to 8 carbon atoms, an aminoalkyl group containing 1 to 7 carbon atoms, a guanidyl-N-alkyl group containing 2 to 4 carbon atoms, an alkyl-mercaptoalkyl group containing 2 to 8 carbon atoms, a carboxyalkyl group containing 2 to 8 carbon atoms, an aryl group, especially phenyl, an aralkyl group, especially phenyl-($C_1$-$C_4$)alkyl, or a substituted aralkyl group, and Y is a group —$CH_2OH$, a group —$COR_2$ or a group —$CH_2COR_2$ where $R_2$ is as defined above, n is zero or 1, and the asymmetric carbon atoms present in the compound may take the R-configuration or the S-configuration or a combination thereof, in an amount effective to produce analgesia, in combination with a pharmaceutically acceptable carrier for said compound.

The compounds of the above formula (I) have such a moiety in their chemical structure which is common to that of bestatin, namely (2S,3R)-3-amino-2-hydroxy-4-phenylbutanoyl-(S)-leucine (see U.S. Pat. Nos. 4,029,547 and 4,189,604), and hence they may be said to be the bestatin-related compounds in brief.

Suitable examples of the compound of the formula (I) used according to this invention are listed in the following table.

TABLE 1

| Compound No. | Compound Name | Abbreviation |
|---|---|---|
| 1 | (2S,3R)-3-amino-2-hydroxy-4-phenylbutanoyl-(S)-leucine | AHPA—L-Leu (= Bestatin) |

TABLE 1-continued

| Compound No. | Compound Name | Abbreviation |
| --- | --- | --- |
| 2 | (2S,3R)-3-amino-2-hydroxy-4-phenylbutanoyl-(R)-leucine | AHPA—D-Leu |
| 3 | (2S,3R)-3-amino-2-hydroxy-4-phenylbutanoyl-(R)-glutamic acid | AHPA—D-Glu |
| 4 | (2S,3R)-3-amino-2-hydroxy-4-phenylbutanoyl-(R)-alanine | AHPA—D-Ala |
| 5 | (2S,3R)-3-amino-2-hydroxy-4-phenylbutanoyl-(R)-arginine | AHPA—D-Arg |
| 6 | (2S,3R)-3-amino-2-hydroxy-4-phenylbutanoyl-(R)-methionine | AHPA—D-Met |
| 7 | (2S,3R)-3-amino-2-hydroxy-4-phenylbutanoyl-(S)-methionine | AHPA—L-Met |
| 8 | (2S,3R)-3-amino-2-hydroxy-4-p-hydroxyphenylbutanoyl-(S)-leucine | p-OH—AHPA—L-Leu |
| 9 | (2S,3R)-3-amino-2-hydroxy-4-p-hydroxyphenylbutanoyl-(R)-leucine | p-OH—AHPA—D-Leu |
| 10 | (2S,3R)-3-amino-2-hydroxy-4-p-hydroxyphenylbutanoyl-(R)-phenylalanine | p-OH—AHPA—D-Phe |
| 11 | (2S,3R)-3-amino-2-hydroxy-4-phenylbutanoyl-(S)-leucyl-(R)-leucine | AHPA—L-Leu—D-Leu |
| 12 | (2S,3R)-3-amino-2-hydroxy-4-phenylbutanoyl-$\beta$-alanine | AHPA—$\beta$-Ala |
| 13 | (2S,3R)-3-amino-2-hydroxy-4-phenylbutanoyl-(R)-asparagine | AHPA—D-Asp |
| 14 | (2S,3R)-3-amino-2-hydroxy-4-phenylbutanoyl-glycine | AHPA—Gly |
| 15 | (2S,3R)-3-amino-2-hydroxy-4-phenylbutanoic acid | AHPA |
| 16 | (2S,3R)-3-amino-2-hydroxy-4-phenylbutanoic acid amide | AHPA—Amide |
| 17 | (2S,3R)-3-amino-2-hydroxy-4-phenylbutanoic acid methyl-ester | AHPA—Me—Ester |
| 18 | (2S,3R)-3-amino-2-hydroxy-4-phenyl-1-butanol | AHPA—1-ol |

Amongst the compounds listed in Table 1 above, the compound Nos. 1 to 10, 12, 13 and 14 are in the form of dipeptide. The compound Nos. 2, 3, 4, 5, 6, 7, 8, 9, 10, 12, 13 and 14 are preferred in this invention.

According to a preferred embodiment of this invention, therefore, there is provided a pharmaceutical composition, useful as analgesic agent, comprising as the active ingredient a dipeptide compound of the formula (Ia)

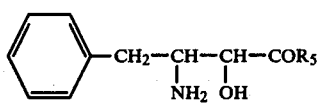

wherein $R_5$ is selected from D-leucine residue, D-glutamic acid residue, D-alanine residue, D-arginine residue, D-methionine residue, L-methionine residue, $\beta$-alanine residue, D-asparatic acid residue and glycine residue, in an amount effective to produce analgesia, in combination with a pharmaceutically acceptable carrier for the active ingredient. These peptide residues are represented by the following formulae.

D-Leucine residue:
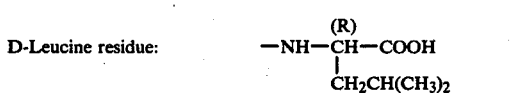

D-Glutamic acid residue:
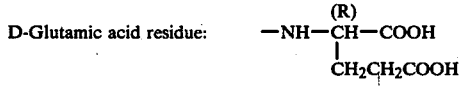

D-Alanine residue:

D-Arginine residue:
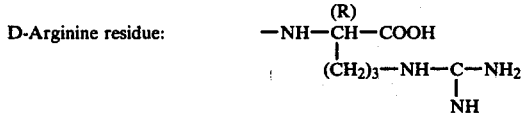

D-Methionine residue:
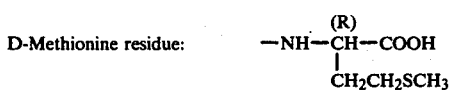

L-Methionine residue:
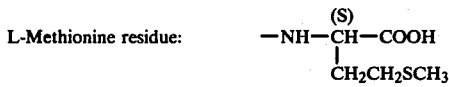

-continued $\beta$-Alanine residue: $-NH-CH_2CH_2COOH$

D-Aspartic acid residue:
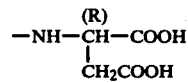

Glycine residue: $-NH-CH_2-COOH$

The compound of the formula (Ia) above includes the compound Nos. 2 to 7, 12, 13 and 14 listed in Table 1 before.

According to a second preferred embodiment of this invention, there is provided a pharmaceutical composition, useful as analgesic agent, comprising as the active ingredient a compound of the formula

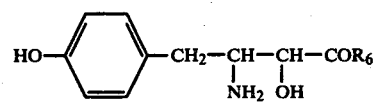

wherein $R_6$ is selected from D-leucine residue of the formula as defined above, L-leucine residue of the formula

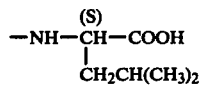

and D-phenylalanine residue of the formula

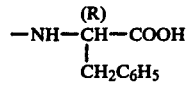

in an amount effective to produce analgesia, in combination with a pharmaceutically acceptable carrier for the active ingredient.

The compound of the above formula (Ib) includes the compound Nos. 8, 9 and 10 listed in Table 1 before.

According to a second aspect of this invention, there is provided a method of therapeutically treating an animal feeling pain, including humans feeling pain, which comprises administering to the animal feeling pain, a compound of the formula (I), including a compound of the formula (Ia) or (Ib), in a non-toxic amount sufficient to reduce or eliminate the pain.

According to a third aspect of this invention, there is provided a method of enhancing the analgesic activity of morphine when administered to an animal feeling pain, including humans feeling pain, which comprises administering an effective and non-toxic amount of a compound of the formula (I), including a compound of the formula (Ia) or (Ib), to the animal just before or at the same time when morphine is given to the animal for the analgesic purpose.

The pharmaceutical composition of this invention, owing to its analgesic activity, may be utilized for the analgesic or antinociceptive treatment of pain in animals, including men. The composition of this invention may be given orally, parenterally or intrarectally or even intramedullarily or intraspinally e.g. by intralumbar puncture and may be formulated into a suitable form for the route of administration employed. Composition in the form of injectable solution may contain 0.1% to 10.0% by weight of the compound (I) as active ingredient, and also one or more of a pH-adjuster, buffer, stabilizer, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. The optimal dosage of the compound (I) administered will, of course, depends on the mode of administration, sex, body weight, age, disease conditions of the patients and the treatment aimed. By way of guideline, for men, the unit dosage generally contains from 20 mg to 2 g of the compound (I) which may be given to an adult person one or more times per day.

Almost compounds of the formula (I) used in accordance with this invention are known substances as disclosed in chemical literatures and patent specifications. The substance which constitutes the fundamental structure of the compound of the formula (I) is (2S,3R)-3-amino-2-hydroxy-4-phenylbutanoic acid (abbreviated as AHPA or (2S,3R)-AHPA here) represented by the formula

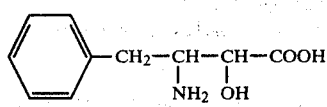

and its steric isomers. It is known that AHPA is obtained by hydrolysis of bestatin with hydrochloric acid (see U.S. Pat. No. 4,189,604 or Japanese patent application prepublication "Kokai" No. 51-7187) and a lower alkyl ester and benzyl ester of AHPA, and amide derivatives of AHPA have been prepared by the present inventors and others.

(2S,3R)-AHPA and its three stereo isomers, namely (2R,3S)-AHPA, (2S,3S)-AHPA and (2R,3R)-AHPA were synthesized by acidolysis of 3-N-benzyloxycarbonylamino-2-hydroxy-4-phenylbutyronitrile, followed by separation procedure as described in U.S. Pat. No. 4,189,604 or Japanese patent application prepublication "Kokai" No. 52-136118. Generally speaking, the compound of the formula (I) above includes the following substances: AHPA; p-hydroxy-AHPA (that is, (2S,3R)-3-amino-2-hydroxy-4-p-hydroxyphenylbutanoic acid described in U.S. Pat. No. 4,189,604 or Japanese patent application prepublication "Kokai" No. 54-79248); esters and amides of AHPA and p-hydroxy-AHPA, respectively,; the hydroxymethyl derivatives obtained by the reduction of the terminal carboxylic group of AHPA and p-hydroxy-AHPA, respectively; dipeptides and tripeptides obtained by condensation of an amino acid or dipeptide with AHPA or p-hydroxy-AHPA; as well as esters, amides and the hydroxymethyl derivatives derived from the aforesaid dipeptides and tripeptides.

The methods for the preparation of the compounds of the formula (I) are described below. The compound (I) which is of the dipeptide type is obtained by the condensation of an amino acid reagent with AHPA or p-hydroxy-AHPA and may be prepared by a method as described in the "Journal of Medicinal Chemistry" Vol. 20, 510–515 (1977) or "Journal or Antibiotics" Vol. 29, No. 5, 600–601 (1976). The condensation of the amino acid reagent with AHPA is performed at a temperature of $-20°$ C. to $25°$ C. by a known procedure for synthesis of peptides in a known manner, whereupon the functional substituent such as amino group, hydroxyl group, carboxyl group, guanidyl group and mercapto group which should not participate in the condensation reaction may, if necessary, have been protected by a known protective group. The condensation reaction may be achieved according to the carbodiimide method using dicyclohexylcarbodiimide as the condensation agent; according to the active ester method using e.g. hydroxysuccinimide ester, according to the active amide method using imidazole and the like; according to the active azide method using e.g. hydrazine; or according to the mixed acid anhydride method using ethyl chloroformate. The organic solvent in which the condensation is conducted may be those employed for the conventional synthesis of peptides and includes, for example, ethers such as tetrahydrofuran and dioxane; esters such as ethyl acetate; ketones such as acetone; halogenated hydrocarbons such as methylene chloride; amides such as dimethylformamide; and nitriles such as acetonitrile. The protected derivative of the amino acid reagent may preferably be in the form of the acid-addition salt, for example, p-toluenesulfonate or hydrochloride of a lower alkyl or benzyl ester of the amino acid reagent. When AHPA or p-hydroxy-AHPA is condensed with the amino acid reagent having blocked its functional group, for example, by the carbodiimide method, the condensation is achieved preferably in the presence of an organic tertiary amine such as N-methylmorpholine, triethylamine and the like. The removal of the residual amino-protecting group from the condensation product may be done by a deprotecting technique known in the chemistry of peptides. For instance, the amino-protecting aralkyloxycarbonyl group, especially benzyloxycarbonyl group may be removed by catalytic hydrogenolysis in the presence of a palladium catalyst, and the alkoxycarbonyl group such as tert-butoxycarbonyl group may be removed by mild acidolysis with hydrogen bromide in acetic acid, with trifluoroacetic acid or with hydrogen chloride in an organic solvent such as dioxane, tetrahydrofuran and ethyl acetate. The compound of the formula (I) which is of the class of tripeptide is obtained by condensation of a depeptide with AHPA or p-hydroxy-AHPA or by condensation of an amino acid with bestatin in a known manner for the synthesis of conventional synthesis of peptides similarly to the procedures just mentioned above and as disclosed also in the applicant's pending Japanese patent application No. 91691/80 (or copending U.S. patent application Ser. No. 272,211, U.K. patent application No. 8119397, West German patent application No. P 31 26 606.1 or French patent application No. 81 13332).

The compound of the formula (I) which is in the form of ester is obtained by esterification of the terminal carboxylic group of the corresponding amino acid, dipeptide or tripeptide in a conventional manner. Particularly, an alkyl ester and benzyl ester of AHPA as well as the amide derivative of AHPA may be prepared from AHPA by a chemical method as described in the "Journal of Antibiotics" Vol. 29, No. 5, 600–601 (1976), for example. The esterification for this purpose may be performed according to the method of reacting the carboxylic group with a diazoalkane such as diazomethane; according to the method of reacting the carboxylic group with a corresponding, appropriate alcohol in the presence of a mineral acid such as sulfuric acid or hydrochloric acid as catalyst or in the presence of an organic acid such as p-toluenesulfonic acid as catalyst; or according to the method of converting the carboxylic group into an alkaline metal salt or amine salt and reacting the latter with a corresponding alkyl halide, aryl halide or aralkyl halide or substituted aralkyl halide such as benzyl bromide or ethyl iodide, and so on. In this esterification method, the functional groups which are present in the raw material or reagent used in addition to the carboxylic group to be esterified may have been blocked with a known protective group in a known manner, if required. Such functional groups which are required to be blocked are amino group, guanidyl group and carboxylic group (other than the carboxylic group to be esterified intentionally) when the esterification method of reacting the carboxylic group with diazoalkane is employed; or amino group, guanidyl group, carboxylic group (other than the carboxylic group to be esterified intentionally) and thiol group when the esterification method of reacting the carboxylic group with an alcohol in the presence of acid catalyst is employed (see E. Schröder et al: "The Peptide" Vol. 1 (1965) and vol. 2 (1966), Academic Press).

In general, the compound of the formula (I) which is in the form of the amide derivative may be prepared by two methods. The first is the method of converting the compound of the formula (I) in the form of a carboxylic acid into a corresponding alkyl ester and then reacting the resulting alkyl ester derivative with a corresponding amine such as ammonia or a substituted ammonia, and the second is the method of condensing the compound of the formula (I) in the form of a corresponding carboxylic acid with a corresponding amine in a known manner for the conventional synthesis of peptides while dehydration is effected during the condensation reaction. This condensation reaction with dehydration may be achieved by the method using dicyclohexylcarbodiimide as the dehydration agent; by the active amide method using imidazole; by the active azide method using hydrazine; or by the mixed anhydride method using ethyl chloroformate (see M. Bondansky et al: "Peptide Synthesis" (1976), John Wiley & Sons).

The compound of the formula (I) which is in the form of the hydroxymethyl derivative may be obtained by reduction of the terminal carboxylic group of a corresponding compound of the formula (I) having the terminal carboxylic group and may be prepared by the method described in the applicant's pending Japanese patent application No. 91690/80 (or copending U.S. patent application Ser. No. 272,211, U.K. patent application No. 8119397, German patent application No. P 31 26 606.1 or French patent application No. 81 13332).

The high analgesic activity of the compound of the formula (I) used in this invention is now described with reference to the following experiments. To this end, there were tested the compounds represented by the following general formula

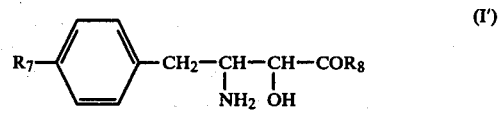

(I')

where $R_7$ and $R_8$ have the meaning as defined in Table 2 below.

TABLE 2

| Compound No. | Compound Abbreviation | $R_7$ | $R_8$ |
|---|---|---|---|
| 1 | AHPA—L-Leu | H | L-leucine residue |
| 2 | AHPA—D-Leu | H | D-leucine residue |
| 3 | AHPA—D-Glu | H | D-glutamic acid residue |
| 4 | AHPA—D-Ala | H | D-alanine residue |
| 5 | AHPA—D-Arg | H | D-arginine residue |
| 6 | AHPA—D-Met | H | D-methionine residue |
| 7 | AHPA—L-Met | H | L-methionine residue |
| 8 | p-OH—AHPA—L-Leu | OH | L-leucine residue |
| 9 | p-OH—AHPA—D-Leu | OH | D-leucine residue |
| 10 | p-OH—AHPA—D-Phe | OH | D-phenylalanine residue |
| 11 | AHPA—L-Leu—D-Leu | H | L-leucyl-D-leucine residue |
| 12 | AHPA—β-Ala | H | β-alanine residue |
| 13 | AHPA—D-Asp | H | D-aspartic acid residue |
| 14 | AHPA—Gly | H | glycine residue |
| 15 | AHPA | H | OH (hydroxyl) |
| 16 | AHPA—Amide | H | $NH_2$ (amino) |
| 17 | AHPA—Me—Ester | H | $OCH_3$ (methoxyl) |

Note: The "L-leucyl-D-leucine residue" in Table 2 is represented by the following formula

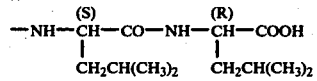

The other amino acid residues shown in Table 2 are as defined in respect of the formulae (Ia) and (Ib) hereinbefore.

The physiological activities of the compound of the formula (I) were determined as follows.

Test 1

Inhibitory activity against enkephalinase were tested.
Testing method:

A preparation of enkephalinase was made by homogenizing corpus striatum of rat brain and by partial purification of the brain homogenate according to the method of Gorenstein et al (see the "Life Science" Vol. 25, 2065–2070 (1979) Pergamon Press, U.S.A.).

A test compound was dissolved in a mixture of Tris-hydrochloride buffered solution (pH 7.7) and an aqueous 1% Triton X100 (an active surfactant) to such a concentration that the added quantity of the test compound amounted to one-tenth of the volume of said mixture. To the solution of the test compound so prepared was added the enkephalinase, followed by incubation for five minutes at ambient temperature and further by addition of methionine-enkephaline as the substrate. The admixture so obtained was incubated at 37° C. for 1 hour and then subjected to a high-performance liquid chromatography in such a manner that the Tyr-Gly-GLy (a fragment of the methionine-enkephaline) formed by the enzymatic degradation of methionine-enkephaline was isolated in some fractions of the eluate and the quantity of Tyr-Gly-GLy was determined by an electro-chemically analysing detector. In this way, $ID_{50}$ value of the test compound, namely the dose of the test compound required for 50% inhibition of the enkephalinase was measured. The test results are shown in Table 3 below.

TABLE 3

Inhibitory activity of test compound of the formula (I') against enkephalinase

| Compound No. | Compound Abbreviation | Inhibitory activity to enkephalinase $ID_{50}$ (milimol) |
|---|---|---|
| 1 | AHPA—L-Leu | 0.62 |
| 2 | AHPA—D-Leu | 2.40 |
| 3 | AHPA—D-Glu | 30.86 |
| 4 | AHPA—D-Ala | 5.98 |
| 5 | AHPA—D-Arg | 0.063 |
| 6 | AHPA—D-Met | 2.54 |
| 7 | AHPA—L-Met | 2.78 |
| 8 | p-OH—AHPA—L-Leu | 0.37 |
| 9 | p-OH—AHPA—D-Leu | 20.68 |
| 10 | p-OH—AHPA—D-Phe | 2.32 |
| 11 | AHPA—L-Leu—D-Leu | 0.95 |
| 12 | AHPA—D-Asp | >32.24 |
| 13 | AHPA—β-Ala | 3.12 |
| 14 | AHPA—Gly | 13.17 |
| 15 | AHPA | 14.00 |
| 16 | AHPA—Amide | 20.50 |
| 17 | AHPA—Me—Ester | 22.80 |

Test 2

Effect of enhancing morphine analgesia was tested.
Testing method:

To Wistar rats (10 week aged, male, body weight 250-300 g) was given intraperitoneally morphine at a dose of 0.5 mg/kg, and these rats receiving the morphine were classified into the group of morphine analgesia-effective rats and the group of morphine analgesia-non-effective rats according to the classification method described in the "Showa Igakukai Zasshi" Vol. 39, No. 5, pages 537–542 (1979). The morphine analgesia-non-effective rats so classified were used as the test animal in this test for estimating the activity of the test compound for enhancement of morphine analgesia. After about 1 week was lapsed since the above classification method, the test procedure of estimating the activity of the test compound for enhancement of morphine analgesia was conducted by administering intraperitoneally 250 mg/kg of the test compound of this invention suspended in water containing 5% gum arabic and 1% Tween 80 (an active surfactant) to the test rats, immediately followed by intraperitoneal administration of 0.5 mg/kg of morphine to these test rats. The effect of analgesia was evaluated according to the method of tail-flick latency of rats described in the "Showa Igakukai Zasshi" Vol. 39, No. 5, pages 537-542 (1979). The evaluation of pain threshold of rats according to the tail-flick latency method was made as follows: Radiant heat stimulus was applied to the region of the rat tail which positioned 1 cm away from the tail tip and which had been colored black with a black-dye, and the time of latency involved in the tail flick, namely the period of time lapsing between the time of application of the heat stimulus and the time of the reflective flick response of the tail was measured. The quantity of the heat applied was so controlled that the average time of latency of the tail-flick response appearing in the control group of rats (receiving not the test compound but the morphine) was about 2.0 seconds. The tests were accomplished as long as the maximum value for the tail-flick latency was 7.0 seconds or less, as otherwise the skin of the rat tail could be damaged by the application of heat. In other words, if the time for the tail-flick latency was longer than 7.0 seconds, the tests were stopped to prevent the damage of the rat tail. The radiant heat stimulus was repeated 5 times for each test rat at an interval of 15 minutes and the times of latency in the flick response of the tail measured in each test were averaged. In each test, 5 rats were used.

The difference in the time of the tail-flick latency between the test rats (receiving 250 mg/kg of the test compound plus 0.5 mg/kg of morphine) and the control rats (receiving 0.5 mg/kg of morphine alone) was calculated, and the effect for enhancement of morphine analgesia was estimated in term of the value of percentages which were calculated by the following equation:

$$\text{Percent of enhancement} = \frac{\text{(Test rat)} - \text{(Control rat)}}{\text{(Control rat)}} \times 100$$

The test results obtained are listed in Table 4 below.

TABLE 4

Effect on enhancement of morphine analgesia

| Compound No. | Test Compound (250 mg/kg + 0.5 mg/kg morphine) | Analgesia enhancement (%) |
|---|---|---|
| 1 | AHPA—L-Leu | 19.5 |
| 2 | AHPA—D-Leu | 24.9 |
| 6 | AHPA—D-Met | 14.7 |
| 7 | AHPA—L-Met | 10.5 |
| 8 | p-OH.AHPA—L-Leu | 34.5 |
| 9 | p-OH.AHPA—D-Leu | 23.1 |
| 10 | p-OH.AHPA—D-Phe | 27.0 |
| 14 | AHPA—Gly | 19.1 |
| 15 | AHPA | 14.1 |
| 5 | AHPA—D-Arg | 13.6 |
| 11 | AHPA—L-Leu—D-Leu | 5.2 |
| 12 | AHPA—1-ol | 12.0 |
| Comparative | Morphine (0.5 mg/kg) | 0 |
| " | Morphine (2 mg/kg) | 28.4 |
| " | Morphine (3 mg/kg) | 35.1 |

Test 3

Analgesic activity of the test compound was tested when it was administered by cisternal puncture into the brain of rats.

Testing method:

Administration of the test compound into the brain was conducted by cisternal puncture (i.e. intracisternal injection) according to the method of Takagi et al described in the "European Journal of Pharmacology" Vol. 55, 109-111 (1979) in such a manner that a J-shaped injection needle was surgically inserted into the brain with the end of said needle remaining in the vicinity of the cisterna magna and that a solution of the test compound in physiological saline was administered intracisternally at a maximum dose of 30 microliters by means of said J-shaped needle into the cisterna magna of unanesthetized test rats after the test rats recovered from the attacks of said surgical operation. The analgesic activity was estimated similarly to Test 2 described above according to the tail-flick latency method but without giving the morphine to the test rats and to the control rats. Analgesic activity was evaluated in term of the value of percentages of increase in the tail-flick latency of the test rats receiving the test compound, as compared to the control rats receiving no test compound. The test results obtained are shown in Table 5 below.

TABLE 5

Analgesic activity of test compound administered alone intracisternally in brain of rat

| Compound No. | Compound Abbreviation | Dose (mcg) | Analgesic activity (%) |
|---|---|---|---|
| 5 | AHPA—D-Arg | 60 | 134.0 |
| 8 | p-OH—AHPA—L-Leu (p-hydroxybestatin) | 500 | 47.0 |

The test as above was repeated with 2 mcg/kg of naloxone (a specific antogonizer to morphine) being intraperitoneally given into the test rats simultaneously to the intracisternal administration of the bestatin-related compound under test. In the latter test, the analgesic activity of the bestatin-related compounds under test disappeared.

As demonstrated above, the compound of the formula (I) used in this invention exhibits an activity inhibitory to enkephalinase and is effective to enhance the analgesic activity of morphine. Some of the compounds of the formula (I) are not significantly effective to enhance the analgesic activity of morphine but they even develop a high analgesic activity when administered intracisternally in the brain, as long as they have a high activity to inhibit enkephalinase in vitro, as the case be with AHPA—D—Arg, for example.

To estimate acute toxicity of the compound of the formula (I), for example, AHPA—D—Ala was injected intraperitoneally into ICR-strain mice (male, 5 week aged, body weight 20 g, 6 mice in each group), and all the mice receiving 2 g/kg of AHPA-D-Ala survived, revealing that the compound of the formula (I) used in this invention is of low toxicity.

From the foregoing, it is clear that the compound of the formula (I) used in this invention is promising as analgesic agent or antinociceptive agent of a new type.

This invention is now described with reference to the following Examples where the preparation of various drugs containing the compound (I) are illustrated. However, these Examples are not limitative of this invention.

EXAMPLE 1

AHPA—D—Arg (10 g) and mannitol (5 g) were dissolved in distilled water to a volume of 1,000 ml, and the resultant aqueous solution was sterilized in a conventional manner. A 2 ml aliquot of the sterilized solution was placed in a glass viral and then freeze-dried. For use, this formulation is dissolved in a sterilized distilled water to make an injectable solution.

EXAMPLE 2

One part (by weight) of p—OH—AHPA—L—Leu and 4 parts (by weight) of lactose were well mixed together and screened through a 50-mesh sieve. The finely divided powder passing the sieve is administrable as a powdery drug.

EXAMPLE 3

One part of p—OH—AHPA—L—Leu, 2.7 parts of lactose, 0.8 parts of corn starch and 0.05 parts of polyvinylpyrolidone (all the parts being by weight) were well mixed each other, and this powdery mixture was granulated by means of a conventional granulator with addition of a volume of ethanol, followed by drying the resultant granules. The granules were mixed with 0.5% of magnesium stearate as lubricant and then compressed in a known manner into tablets each weighing 100 mg.

EXAMPLE 4

One part of AHPA—L—Leu was well mixed with 4 parts of lactose, and the resulting powdery mixture was screened through a 50 mesh-sieve. The finely divided powder passing the sieve is administrable as a powdery drug.

EXAMPLE 5

AHPA—Amide was mixed with lactose, corn starch and polyvinylpyrolidone and then processed into tablets each weighing 100 mg, in a similar way to Example 3 above.

EXAMPLE 6

AHPA—Me—Ester hydrochloride together with mannitol was dissolved in distilled water and then processed in the same manner as in Example 1 above to prepare a lyophilized formulation which is ready for use as injectable solution.

The following Examples 7-8 illustrate the preparation of the new compounds used in this invention which belong to the formula (I).

EXAMPLE 7

(a) Synthesis of (2S,3R)-3-N-benzyloxycarbonylamino-2-hydroxy-4-phenylbutanoyl-(S)-leucyl-(R)-leucine benzylester

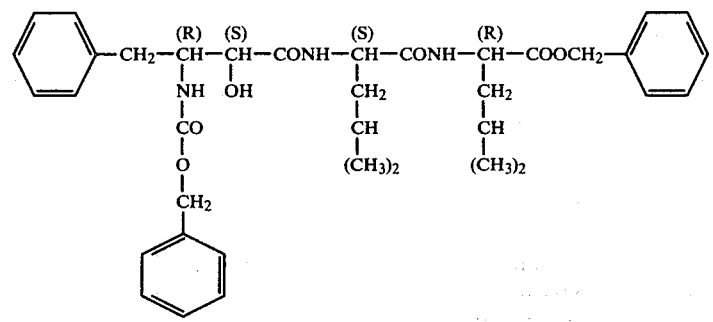

(2S,3R)-3-N-benzyloxycarbonylamino-2-hydroxy-4-phenylbutanoyl-(S)-leucine (1.11 g) and (R)-leucine benzylester p-toluenesulfonate (983.3 mg) were admixed with 3 ml of tetrahydrofuran, followed by addition of 0.3 ml of N-methylmorpholine and 330 mg of N-hydroxysuccinimide. The resulting solution was ice-cooled and then admixed with 670 mg of dicyclohexylcarbodiimide, followed by stirring for 4 hours under ice-cooling. The reaction mixture was filtered to remove the urea derivative as produced, and the filtrate was concentrated to dryness under reduced pressure. The solid residue was dissolved in 15 ml of ethyl acetate and the solution obtained was washed with 9 ml of 1 N hydrochloric acid, 9 ml of 1 N aqueous sodium hydroxide and finally with 9 ml of distilled water. The organic solvent phase was mixed with anhydrous magnesium sulfate for drying and then the mixture was filtered to remove the magnesium sulfate hydrate. The solution (the filtrate) was concentrated to dryness under reduced pressure to give a crude solid of the titled compound. Crystallization of this product from acetoneethylether gave 1.39 g of colorless needles. Mass spectrometry of this pure product gave a value of m/e 646 (M+1).

(b) Synthesis of (2S,3R)-3-amino-2-hydroxy-4-phenylbutanoyl-(S)-leucyl-(R)-leucine (Compound No. 11)

The compound obtained in the above step (a) was taken up into a mixture of 70 ml of dioxane and 1.4 ml of distilled water, and the resultant solution was admixed with 420 mg of palladium black as the hydrogenolysis catalyst. The mixture was subjected to the hydrogenolysis at ambient temperature with hydrogen gas at 3 atm. for 48 hours to effect removal of both the amino-protecting benzyloxycarbonyl group and the carboxyl-protecting benzyl group. The reaction mixture was filtered to remove the catalyst, and the filtrate was concentrated to dryness under reduced pressure. Recrystallization of this powder from methanol gave 510 mg of the titled compound (AHPA-L-Leu-D-Leu) as colorless plate-like crystals. m.p. 240°-243° C. Mass spectrometry: m/e 422. When this product was subjected to a silica gel thin layer chromatography on a silica gel plate (Art. 5715, a product of Merck Co., Germany) developed with a mixed solvent of butyl acetate-n-butanol-acetic acid-water (4:4:1:1 by volume), it showed an Rf value of 0.33.

Elemental analysis: Found: C 63.10, H 8.09, N 9.70%. Calcd. for $C_{22}H_{35}N_3O_5$: C 62.91, H 8.39, N 9.97%.

EXAMPLE 8

(a) Synthesis of (2S,3R)-3-N-t-butoxycarbonylamino-2-hydroxy-4-phenyl-1-butanol

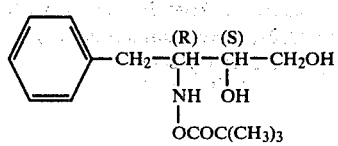

N-t-Butoxycarbonyl-(2S,3R)-3-amino-2-hydroxy-4-phenylbutanoic acid methylester (92.8 mg) was dissolved in 0.44 ml of ethanol, and to the resultant solution was added dropwise at ambient temperature 2.3 ml of ethyl alcohol containing 46.6 mg of sodium borohydride. After this, the mixture was stirred for 2 hours at ambient temperature to effect the reduction of the carboxylate group. After the reaction was completed, the reaction mixture was concentrated to dryness under reduced pressure and the solid residue was taken up into 3 ml of ethyl acetate. The solution obtained was washed with 2 ml of an aqueous solution of 1% citric acid and then with three 2 ml portions of saturated aqueous sodium chloride. The organic solvent phase in the ethyl acetate was dried over magnesium sulfate for the drying purpose, and the mixture was filtered to remove the magnesium sulfate hydrate therefrom. The filtrate was concentrated to dryness to give 81 mg of a crude solid of the titled compound. When this was recrystallized from a mixture of 0.5 ml of ethylether and 0.5 ml of n-hexane, there was obtained 68 mg of colorless needles. m.p. 113°-115° C. This product gave a value of m/e 282 (M+1) in the analysis of mass spectrometry.

Elemental analysis: Found: C 63.69, H 8.31, N 4.70%. Calcd. for $C_{15}H_{23}NO_4$ (molecular weight 281.39): C 64.00, H 8.26, N 4.98%.

(b) Synthesis of (2S,3R)-3-amino-2-hydroxy-4-phenyl-1-butanol (Compound No. 18) hydrochloride The compound (68 mg) obtained in the above step (a) was dissolved in 0.4 ml of dry methanol containing 20% hydrogen chloride under ice-cooling and then allowed to stand for 30 minutes to effect removal of the t-butoxycarbonyl group. The reaction mixture was then concentrated to dryness and the residue was recrystallized from ethanol-ethylether to afford 36 mg of the titled compound (AHPA-1-ol) as colorless plate-like crystals. m.p. 123°-125° C. $[\alpha]_D^{25}$ +28.4° (c 1.0, 1 N-HCl). This product gave a value of m/e 182 in the analysis of mass spectrometry.

Elemental analysis: Found: C 54.93, H 7.46, N 6.40, Cl 16.0%. Calcd. for $C_{10}H_{16}NO_2Cl$ (molecular weight 217.72): C 55.30, H 7.42, N 6.44, Cl 16.3%.

What we claim is:

1. A method of therapeutically treating an animal feeling pain which comprises administering to the animal a compound of the formula (I):

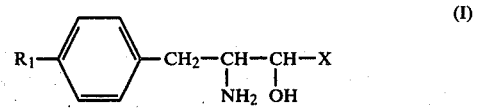

wherein $R_1$ denotes a hydrogen atom or a hydroxyl group, X denotes a group —$COR_2$ where $R_2$ is a hydroxyl group, a lower alkoxy group, a benzyloxy group, an amino group or a lower alkyl mono- or di-substituted amino group, or X denotes a group —$CH_2OH$, a group —CONH—CH—Y or a
                |
                $R_3$

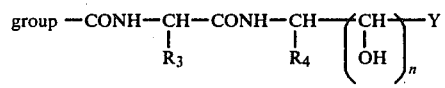

where $R_3$ and $R_4$ are equal to each other or are different from each other and are each a hydrogen atom, an alkyl group of 1 to 7 carbon atoms, a hydroxyalkyl group containing 1 to 7 carbon atoms, a mercaptoalkyl group containing 1 to 7 carbon atoms, a carboxyamidoalkyl group containing 2 to 8 carbon atoms, an aminoalkyl group containing 1 to 7 carbon atoms, a guanidyl-N-alkyl group containing 2 to 4 carbon atoms, an alkylmercaptoalkyl group containing 2 to 8 carbon atoms, a carboxylalkyl group containing 2 to 8 carbon atoms, an aryl group, especially phenyl, an aralkyl group, especially phenyl-($C_1$-$C_4$)alkyl, or a substituted aralkyl group, and Y is a group —$CH_2OH$, a group —$COR_2$ or a group —$CH_2COR_2$ where $R_2$ is as defined above, n is zero or 1, and the asymmetric carbon atoms present in the compound may take the R-configuration or the S-configuration or a combination thereof in a non-toxic amount sufficient to reduce or eliminate the pain.

2. A method of enhancing the analgesic activity of morphine when administered to an animal feeling pain, which comprises administering an effective and non-toxic amount of the compound of the formula (I)

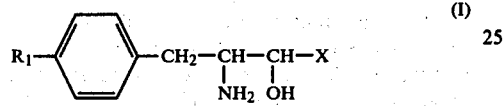

wherein $R_1$ denotes a hydrogen atom or a hydroxyl group, X denotes a group —$COR_2$ where $R_2$ is a hydroxyl group, a lower alkoxyl group, a benzyloxy group, an amino group or a lower alkyl mono- or di-substituted amino group, or X denotes a group —$CH_2OH$, a group —CONH—CH—Y or a
　　　　|
　　　　$R_3$

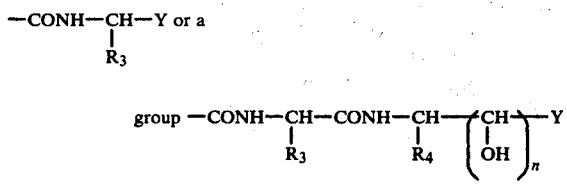

where $R_3$ and $R_4$ are equal to each other or are different from each other and are each a hydrogen atom, an alkyl group of 1 to 7 carbon atoms, a hydroxyalkyl group containing 1 to 7 carbon atoms, a mercaptoalkyl group containing 1 to 7 carbon atoms, a carboxamidoalkyl group containing 2 to 8 carbon atoms, an aminoalkyl group containing 1 to 7 carbon atoms, a guanidyl-N-alkyl group containing 2 to 4 carbon atoms, an alkylmercaptoalkyl group containing 2 to 8 carbon atoms, a carboxyalkyl group containing 2 to 8 carbon atoms, an aryl group, especially phenyl, an aralkyl group, especially phenyl-($C_1$-$C_4$) alkyl, or a substituted aralkyl group, and Y is a group —$CH_2OH$, a group —$COR_2$ or a group —$CH_2COR_2$ where $R_2$ is as defined above, n is zero or 1, and the asymmetric carbon atoms present in the compound may take the R-configuration or the S-configuration or a combination thereof to the animal just before or at the same time as when morphine is given to the animal for the analgesic purpose.

3. A method as claimed in claim 1 wherein the active ingredient is a compound of the formula (Ia):

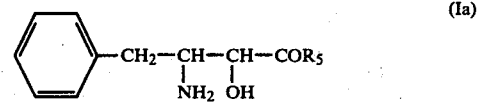

wherein $R_5$ is selected from D-leucine residue, D-glutamic acid residue, D-alanine residue, D-arginine residue, D-methionine residue, L-methionine residue, β-alanine residue, D-asparatic acid residue and glycine residue.

4. A method as claimed in claim 1 wherein the active ingredient is a compound of the formula (Ib):

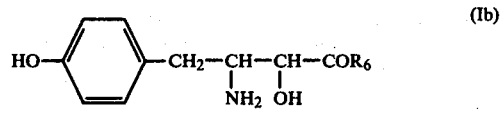

wherein $R_6$ is selected from D-leucine residue, L-leucine residue and D-phenylalanine residue, in an amount effective to produce analgesis.

5. A method as claimed in claim 2 wherein the active ingredient is a compound of the formula (Ia):

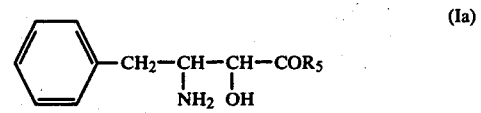

wherein $R_5$ is selected from D-leucine residue, D-glutamic acid residue, D-alanine residue, D-arginine residue, D-methionine residue, L-methionine residue, β-alanine residue, D-asparatic acid residue and glycine residue.

6. A method as claimed in claim 2 wherein the active ingredient is a compound of the formula (Ib):

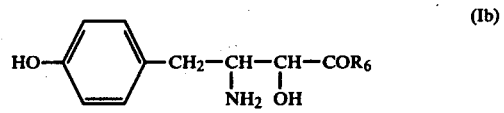

wherein $R_6$ is selected from D-leucine residue, L-leucine residue and D-phenylalanine residue, in an amount effective to produce analgesia.

* * * * *